United States Patent
Cates et al.

(10) Patent No.: US 7,331,981 B2
(45) Date of Patent: *Feb. 19, 2008

(54) BLOOD VESSEL SEALING SYSTEM

(75) Inventors: Christopher U. Cates, Dunwoody, GA (US); William D. Knopf, Atlanta, GA (US); Douglass G. Whitney, Roswell, GA (US)

(73) Assignee: CCH Associates, LLC, Hiawassee, GA (US)

( * ) Notice: Subject to any disclaimer, the term of this patent is extended or adjusted under 35 U.S.C. 154(b) by 707 days.

This patent is subject to a terminal disclaimer.

(21) Appl. No.: 10/791,196

(22) Filed: Mar. 2, 2004

(65) Prior Publication Data

US 2004/0172060 A1    Sep. 2, 2004

Related U.S. Application Data

(63) Continuation of application No. 09/656,643, filed on Sep. 7, 2000, now Pat. No. 6,699,261, which is a continuation of application No. 08/383,256, filed on Feb. 3, 1995, now Pat. No. 6,162,240, which is a continuation of application No. 07/817,587, filed on Jan. 7, 1992, now Pat. No. 6,056,768.

(51) Int. Cl.
  *A61B 19/00* (2006.01)

(52) U.S. Cl. ........................................... 606/213

(58) Field of Classification Search ........... 606/213, 606/214, 108
See application file for complete search history.

(56) References Cited

U.S. PATENT DOCUMENTS

| | | |
|---|---|---|
| 1,432,482 A | 10/1922 | Merriam |
| 1,563,881 A | 1/1925 | Velter |
| 2,647,294 A | 8/1953 | Davis |
| 3,223,083 A | 12/1965 | Cobey |
| 4,645,488 A | 2/1987 | Matukas |
| 4,744,364 A | 5/1988 | Kensey |
| 4,790,819 A | 12/1988 | Li et al. |
| 4,852,568 A | 8/1989 | Kensey |
| 4,871,094 A | 10/1989 | Gall et al. |
| 4,874,368 A | 10/1989 | Miller et al. |
| 4,890,612 A | 1/1990 | Kensey |
| 4,909,251 A | 3/1990 | Seelich |
| 4,929,246 A | 5/1990 | Sinofsky |

(Continued)

FOREIGN PATENT DOCUMENTS

AU    B-12498/92    9/1992

OTHER PUBLICATIONS

"Fibrijet™ Surgical Sealant Delivery Systems," published by Micromedics, Inc., publication date unknown.

(Continued)

*Primary Examiner*—Michael Thaler
(74) *Attorney, Agent, or Firm*—King & Spalding LLP

(57) ABSTRACT

A method of and apparatus for sealing access openings into blood vessels using an expandable member in the blood vessel on a control member that extends out through the access opening and an applicator which inserts a preformed sealing material into the access opening over the control member to keep the control member and expandable member centered in the access opening and withdrawing the collapsed expandable member back through the sealing material after the access opening is sealed.

1 Claim, 6 Drawing Sheets

U.S. PATENT DOCUMENTS

| | | |
|---|---|---|
| 5,021,059 A | 6/1991 | Kensey |
| 5,053,046 A | 10/1991 | Janese |
| 5,108,421 A | 4/1992 | Fowler |
| 5,129,882 A | 7/1992 | Weldon et al. |
| 5,141,515 A | 8/1992 | Eberbach |
| 5,147,316 A | 9/1992 | Castillenti |
| 5,290,310 A | 3/1994 | Makower et al. |
| 5,320,639 A | 6/1994 | Rudnick |
| 5,370,660 A | 12/1994 | Weinstein et al. |
| 5,383,899 A | 1/1995 | Hammerslag |
| 5,391,183 A | 2/1995 | Janzen et al. |
| 5,419,765 A | 5/1995 | Weldon et al. |

OTHER PUBLICATIONS

"The Only Vascular Sealing Device With Thrombin," published by Vascular Solutions, Inc., published on or about June of 2000.

"What is Vasoseal® ?," published by Datascape Collagen Products, published on or before May 5, 2000.

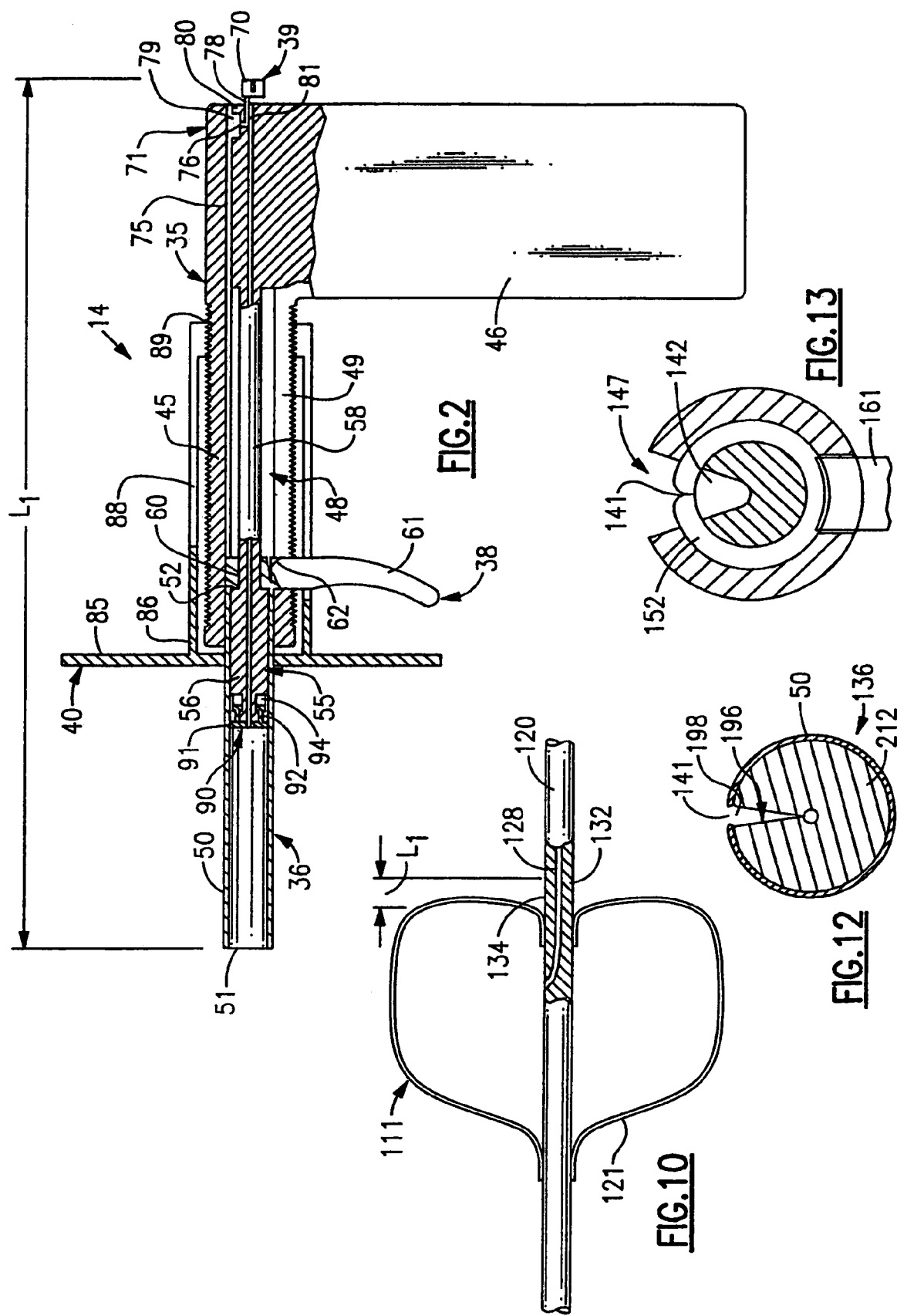

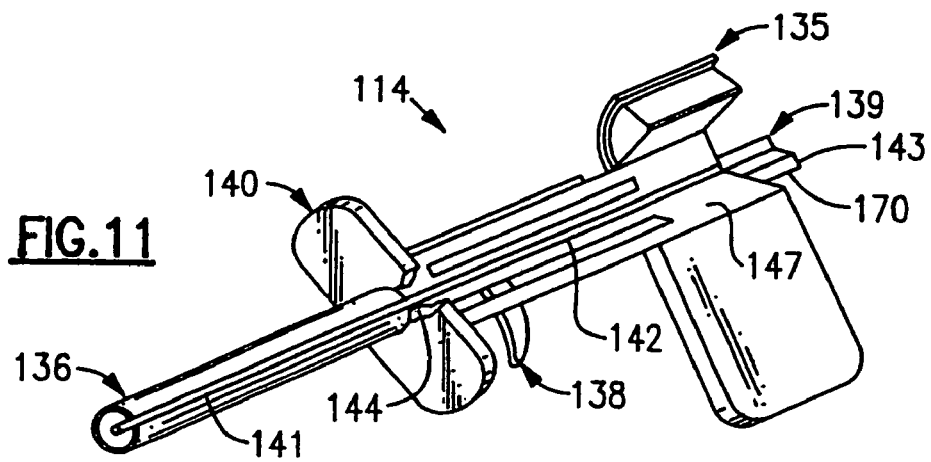
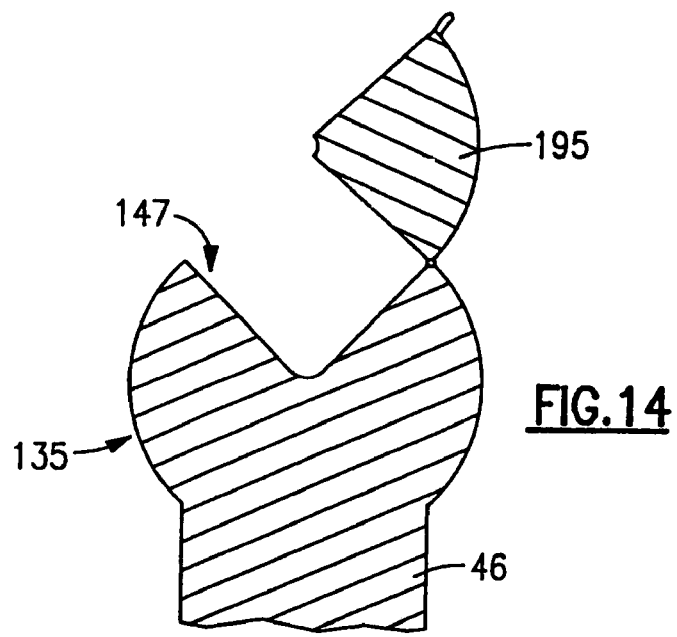
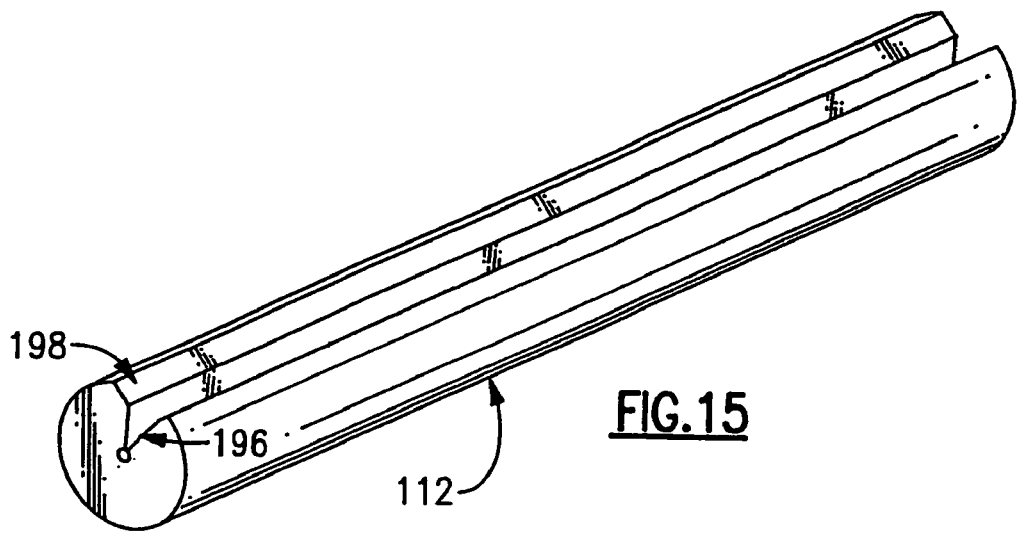

BLOOD VESSEL SEALING SYSTEM

CROSS-REFERENCE TO RELATED APPLICATIONS

This is a continuation of prior U.S. patent application Ser. No. 09/656,643 filed Sep. 7, 2000 (now U.S. Pat. No. 6,699,261), which is a continuation of U.S. patent application Ser. No. 08/383,256 filed Feb. 3, 1995 (now U.S. Pat. No. 6,162,240) which is a continuation of U.S. patent application Ser. No. 07/817,587 filed Jan. 7, 1992 (now U.S. Pat. No. 6,056,768), the disclosures of which are incorporated herein by reference in their entirety.

BACKGROUND OF THE INVENTION

This invention relates generally to the stopping of bleeding from blood vessels through openings in the vessel wall and more particularly through surgically produced punctures for different medical procedures.

Certain medical procedures require the percutaneous puncturing of a blood vessel to gain access to the interior of the vascular system of the patient for the procedure to be conducted. Procedures that commonly require such an percutaneous punctures are balloon angioplasty procedures, arteriography, venography, angiography and other diagnostic procedures that use blood vessel catheterization. Typically the percutaneous opening or puncture is made into a relatively large blood vessel such as a femoral artery. One of the difficulties in these procedures, however, is reclosure of the opening in the blood vessel wall after the procedure. In the past, manual pressure and/or mechanical clamping pressure have been used to physically hold the opening closed until a blood clot formed with sufficient strength to keep the opening blocked until healing takes place. More recently, several techniques have been used to insert a collagen plug in the tissue access passage to the blood vessel that promotes the formation of a coagulum at the vessel wall opening.

One such prior art technique simply inserts the collagen plug into the access passage in the tissue to the vessel wall puncture. The difficulty with this procedure is that there is no practical way to positively limit the protrusion of the collagen into the interior of the blood vessel. This sometimes results in the collagen being inserted or subsequently expanding through the blood vessel wall opening into the vessel lumen and causing a blood clot to form in the interior of the blood vessel. This is undesirable because the clot and/or the protruding collagen can dislodge and move along the blood vessel to cause an embolus. Also, the clot formed at the interior end of the puncture site can serve to undesirably restrict the blood flow past the site (i.e. thrombosis).

Another technique is to insert a sealing plug through the opening in the blood vessel wall with a first orientation and then turned to an orientation such that it will not pass back out through the opening. The sealing plug is manipulated by a lanyard which extends back out through the tissue access passage exteriorly of the patient's body to be manually held. The collagen plug is then passed down over the lanyard while the sealing plug is manually held in the blood vessel wall opening. Enough seepage of blood around the sealing plug is present to form the clot at the blood vessel wall opening. The sealing plug is left in position in the blood vessel wall and is made out of a material which is absorbable by the body over a several weeks or months period. The problem with this technique is that the sealing plug may break loose before it is absorbed by the body and cause a blockage of the blood flow through the blood vessel. The sealing plug may be a nidus for a blood clot to form and subsequently dislodge resulting in embolization. Another potential problem in leaving a device inside the vessel wall is that the device, like any foreign body, may erode the wall of the vessel or promote extensive intravascular scaring both of which potentially will disrupt vessel architecture.

SUMMARY OF THE INVENTION

These and other problems and disadvantages associated with the prior art are overcome by the invention disclosed herein by providing a technique for implanting a collagen plug in the tissue access passage to the percutaneous puncture or opening in a blood vessel which insures that the end of the plug does not extrude through the blood vessel wall opening into the blood vessel lumen. A tamponading means located inside the blood vessel lumen during installation of the collagen plug serves to positively prevent the collagen plug from being inadvertently pushed through the blood vessel wall opening as it is installed but which is removed after installation of the collagen plug so that no protrusion or other dislodgable material is left in the interior of the blood vessel after the procedure is completed. The tamponading means is selectively expandable to an expanded size and shape such that it will not pass back out through the blood vessel wall opening and its position in the blood vessel is controlled by a control member extending exteriorly of the patient for easy manipulation. For removal, however, tamponading means is selectively collapsible to a collapsed condition small enough to pass back out through the installed collagen plug without interfering with the coagulum forming capability of the collagen plug. The technique is simple to use and the location of the collagen plug is inherently accurately positioned at the blood vessel wall opening independently of variances in the patient's skin and tissue thickness at the puncture site and without premeasuring or adjustment of the applicator.

The method of the invention is directed to the sealing a percutaneous puncture through a blood vessel wall comprising the steps of inserting a collapsed expandable tamponading member attached to a control member into the blood vessel lumen through the blood vessel wall puncture so that the control member extends out of the patient through the access passage to the skin surface; expanding the tamponading member to a size larger than the blood vessel wall puncture; pulling the expanded tamponading member back against the blood vessel wall opening using the control member to form a seal at the interior end of the blood vessel wall puncture; inserting a collagen plug into the access passage around the control member while the seal is maintained at the blood vessel wall puncture until the leading end of the collagen plug is located at the exterior end of the blood vessel wall puncture; then collapsing the tamponading member to the collapsed condition; and retracting the collapsed tamponading member back through the collagen plug. The collagen plug has a preformed passage therethrough which slidably receives the control member to allow placement of the collagen plug along the control member. The collagen serves to induce a coagulum that seals the outside end of the puncture in the blood vessel wall. After the collapsed tamponading member is pulled back through the collagen plug, the collagen plug self seals any opening through the plug left by the passage of the expandable member. The collagen plug may be housed in a retractable barrel while the collagen plug is inserted into the access passage and the barrel then retracted from around the collagen plug while maintaining the collagen plug in a substantially fixed position in the access passage. The barrel may be retracted fully or partially from around the collagen plug before the expanded tamponading member is collapsed and withdrawn. The method may also include visually indicating when the projecting end of the collagen plug is located at the exterior end of the blood vessel puncture. The collagen plug may also be backed up while the collapsed tamponading member is withdrawn through the plug to insure that the plug remains in place. The collagen plug may also be urged slightly toward the blood vessel wall puncture to compensate for any loss in volume of the collagen plug as it turns into a gelatinous mass.

The apparatus of the invention comprises a temporary sealing arrangement including an elongate flexible control portion small enough to pass through the blood vessel wall puncture with an expandable tamponading portion on the projecting end of the control portion collapsible to a condition smaller than the blood vessel wall puncture and expandable to a condition larger than the blood vessel wall puncture so that it will not easily pull back through the puncture. An applicator is provided to install the collagen plug in the access passage through the skin and tissue of the patient down to the exterior end of the blood vessel wall. The applicator cooperates with the control portion of the temporary sealing arrangement to fixedly locate the applicator with respect to the exterior end of the blood vessel wall and facilitate the positioning of the collagen plug with respect to the exterior end of the blood vessel wall puncture. The applicator includes a plug carrying assembly with a prescribed length used to insert the collagen plug. The control portion of the sealing arrangement includes indicia spaced a prescribed locating distance from that side of the expanded tamponading portion facing the puncture to provide a visual indication that the leading end of the collagen plug is located at the exterior end of the blood vessel wall puncture. The plug carrying assembly has an installation barrel defining a plug carrying chamber therein adapted to receive the collagen plug for installation in the access passage and a retraction arrangement is provided for selectively retracting the installation barrel from around the collagen plug while maintaining the plug at a substantially fixed position relative to the exterior end of the blood vessel wall puncture. The applicator may have a tightening mechanism for pulling the expanded tamponading portion of the temporary sealing arrangement tighter against the blood vessel wall puncture as the installation barrel is withdrawn from around the collagen plug. The applicator may also have an urging mechanism for urging the exterior end of the collagen plug toward the blood vessel wall with a slight force just sufficient to offset volume loss as the collagen plug softens to a gelatinous mass on contact with body fluids. This is especially true while the collapsed tamponading member is being withdrawn. The expanded tamponading portion of the sealing arrangement may be an inflatable balloon with an inflation lumen through the control portion for use in selectively inflating the balloon to the expanded condition.

These and other features and advantages of the invention will become more clearly understood upon consideration of the following detailed description and accompanying drawings wherein like characters of reference designate corresponding parts-throughout the several views and in which:

BRIEF DESCRIPTION OF THE DRAWINGS

FIG. 2 is an enlarged longitudinal cross-sectional view of the applicator;

FIG. 10 is an enlarged longitudinal cross-sectional view of another embodiment of the expandable tamponading member;

FIG. 11 is a perspective view of a second embodiment of the invention;

FIG. 12 is an enlarged transverse cross-sectional view taken along line 12-12 in FIG. 11;

FIG. 13 is an enlarged transverse cross-sectional view taken along line 13-13 in FIG. 11;

FIG. 14 is an enlarged transverse cross-sectional view taken along line 14-14 in FIG. 11;

FIG. 15 is an enlarged perspective view of the collagen plug used in that embodiment of the applicator seen in FIGS. 11-14;

These figures and the following detailed description disclose specific embodiments of the invention, however, it is to be understood that the inventive concept is not limited thereto since it may be embodied in other forms.

DETAILED DESCRIPTION OF ILLUSTRATIVE EMBODIMENTS

The blood vessel sealing system 10 is used to stop the bleeding from a percutaneous puncture BVP made in the wall BVW of a blood vessel BV as an incident to a medical procedure. Typically, the blood vessel BV used is a femoral artery in the groin region with a relatively large vessel passage or lumen BVL to facilitate locating the blood vessel and permits a sufficiently large puncture to be made through the wall BVW thereof to carry out the procedure. Medical procedures which are typically performed through such an puncture are angioplasty and other procedures which pass a catheter or other type probe into and along the blood vessel lumen BVL. When such a procedure is performed, an initial percutaneous puncture with an appropriate needle is made from the patient's skin through the tissue and the blood vessel wall into the blood vessel lumen and a guide wire installed. The needle is then removed leaving the guide wire in place and a tapered introducer guide sheath GS is installed over the guide wire to enlarge that portion of the puncture through the skin and tissue into an access passage AP while the blood vessel wall puncture BVP remains at about the original puncture size. The guide sheath GS serves to keep the passage open and prevent further damage to the tissue and skin around the passage. The guide sheath GS is removed after the procedure is completed. This sheath GS assists in the installation of the sealing system 10 as will become more apparent.

Figure 1:
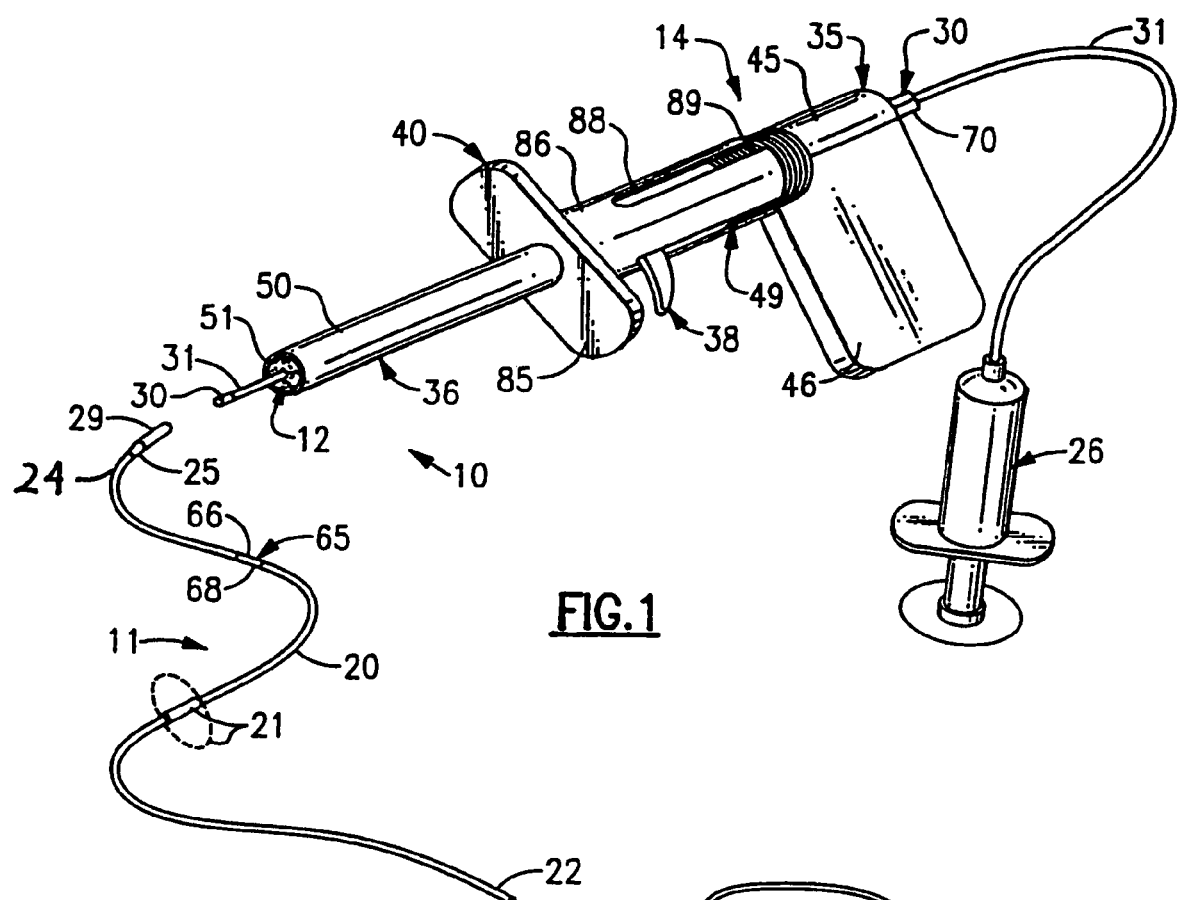
FIG. 1 is a perspective view of a first embodiment of the invention.

Referring to FIG. 1, it will be seen that the sealing system 10 embodying the invention includes generally a temporary sealing assembly 11, a collagen plug 12 and an applicator 14. The sealing assembly 11 is inserted into the blood vessel lumen BVL through the introducer guide sheath GS and then the sheath removed leaving the sealing assembly in place. The sealing assembly 11 serves to temporarily seal the interior end of the puncture BVP in the blood vessel wall BVW while the collagen plug 12 is placed in the access passage AP to the exterior end of the puncture BVP. After the collagen plug 12 is installed, the temporary sealing assembly 11 is removed through the collagen plug to insure that nothing protrudes into the blood vessel lumen BVL to cause problems later. The applicator 14 serves to install the collagen plug 12 in the access passage AP around the temporary sealing assembly 11 so the collagen plug 12 can cause a coagulum to form at the exterior end of the blood vessel wall puncture BVP and stop the bleeding through the puncture.

The sealing assembly 11 includes an elongate flexible control member 20 on which is mounted an expandable tamponading member 21. The control member 20 is designed for the projecting end 22 thereof to pass through the guide sheath GS in the access passage AP and then through the puncture BVP in the blood vessel wall BVW into the blood vessel lumen BVL while the opposite end 24 thereof remains exteriorly of the patient. The projecting end 22 extends through the tamponading member 21 sufficiently for the control member 20 to still extend into the blood vessel lumen BVL after the tamponading member is removed from the patient so that the tamponading member 21 can be reinserted if necessary in the event of a failure. The exterior end 24 of the member 20 is provided with a coupling 25 for connection to an expanding mechanism 26 for selectively expanding the tamponading member 21 from a collapsed condition as seen by solid lines in FIG. 1 closely adhering to the control member outside surface to an expanded condition as will become more apparent.

Figure 3:
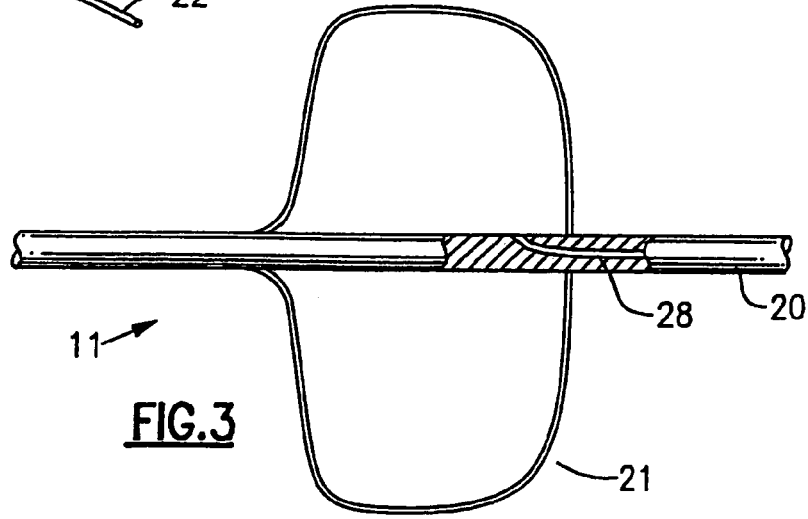
FIG. 3 is an enlarged longitudinal cross-sectional view of the expandable tamponading member.

It will be appreciated that the tamponading member 21 may be mechanically, electrically, pneumatically or hydraulically expanded and collapsed without departing from the scope of the invention. The particular expanded exterior configuration of the tamponading member 21 can be selected depending on the particular circumstances of use. The configuration may be elongated in one direction and/or may have a flattened side facing the blood vessel wall puncture BVP after the tamponading member 21 is located in the blood vessel lumen BVL. The criteria that is used to determine the particular size and configuration is the blood vessel condition at the puncture BVP and the cross-sectional size and shape of the blood vessel lumen BVL in the vicinity of the puncture BVP. The largest cross-sectional dimension of the expanded tamponading member 21 must be small enough for the member 21 to be pulled back against the interior end of the puncture BVP without dragging or hanging up in the blood vessel lumen BVL. It has been found that an expanded dimension in one direction for the member 21 that is at least about 1.5 times larger than the puncture BVP is satisfactory to prevent the tamponading member 21 from being pulled back through the puncture BVP under typical conditions. That portion of the tamponading member 21 at the puncture BVP must be larger than the size of the puncture BVP to insure sealing when the tamponading member 21 is pulled back up against the interior end of the puncture BVP as will become more apparent. While different expanded sizes may be used, dimensions on the order of 0.150-0.200 inch (3.8-5.1 mm) should be successful under typical conditions where the puncture BVP is made with a 4 french puncture. Without limiting the scope of the invention, the particular tamponading member 21 illustrated in FIG. 3 is a small inflatable balloon which can be inflated to a size and configuration sufficiently larger than the blood vessel wall puncture BVP to prevent the expanded balloon member 21 from being pulled back through the puncture BVP while at the same time not hanging up in the blood vessel lumen BVL in its expanded condition. In the expanded condition, the member 21 has a puncture facing side that is substantially normal to the centerline of the control member 20. The inflatable balloon member 21 may be made out of any suitable material such as latex. The balloon member 21 is inflated and deflated through the control member 20 as will become more apparent.

Figure 4:
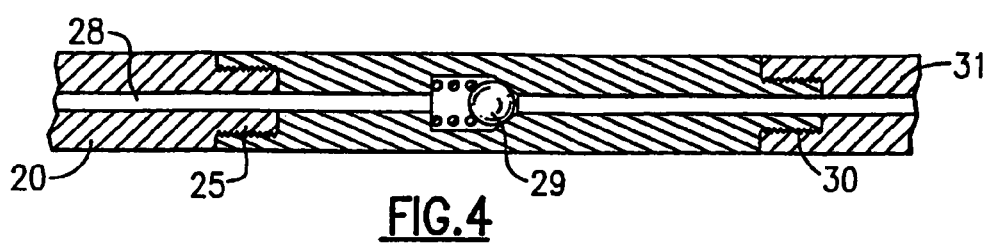
FIG. 4 is an enlarged longitudinal cross-sectional view of the coupling arrangement on the end of the control member.

The control member 20 is a thin elongate member similar in size and flexibility to the guide wire used to originally install the sheath GS in the access passage AP. The control member 20 is sufficiently long to extend from within the blood vessel lumen BVL out through the puncture BVP and the access passage AP exteriorly of the patient so that it can be manually manipulated and is also long enough that the guide sheath GS can be removed while manually holding the expanded tamponading member 21 in place over the puncture BVP to maintain the seal. To permit the balloon member 21 to be inflated, the control member 20 defines an inflation lumen 28 therein seen in FIGS. 3 and 4 that extends from and communicates with the interior of the balloon member 21 along the length of the member 20 and opens out through the coupling 25. Thus, the balloon tamponading member 21 can be inflated and deflated through the lumen 28 from a position external to the patient.

The balloon member 21 is inflated by any convenient fluid inflation device such as the syringe 26 illustrated. Typically, the syringe 26 or other inflation device will be of the same type as that already used in balloon angioplasty and has an extension 31 sized similarly to the control member equipped with a mating coupling 30 to be selectively connected to the coupling 25 on the end of the control member 20. The inflation fluid under pressure from the syringe 26 flows along the inflation lumen 28 in the control member 20 into the balloon member 21 to inflate same.

In those instances where it is necessary to remove the inflation device 26 after the balloon member 21 is inflated to the expanded condition to complete the insertion of the collagen plug into the access passage AP, the balloon member 21 can be maintained inflated by providing a check valve 29 on the exterior end 24 of the control member 20. The check valve 29 may be incorporated in the coupling 25 or be a separate member as shown in the drawings at FIG. 4. To deflate the balloon member 21 after the procedure is complete, the physician can insert a needle into the valve 29 to open it or if the valve is a separate member, the valve 29 can simply be removed from the coupling 25. The outside diameter of the member 20 including the coupling 25 and the check valve 29 should be as small as possible in order to pass freely through the puncture BVP and to pass through the collagen plug 12 without significantly disturbing it. While different diameters may be used, diameters of 0.030-0.050 inch (0.8-1.3 mm) are satisfactory.

The applicator 14 best seen in FIGS. 1 and 2 includes a housing assembly 35 which mounts an introducer assembly 36 to house the collagen plug 12 while it is inserted into the access passage AP. A retraction mechanism 38 withdraws the introducer assembly 36 from around the collagen plug 12 after it is inserted in the patient. An interconnect assembly 39 interconnects the control member 20 and the applicator 14 to positively locate the tamponading member 21 with respect to the introducer assembly 36 is being withdrawn from around the collagen plug. A locator mechanism 40 is provided on the housing assembly 35 to be adjusted for a secondary fixed point of reference as the introducer assembly 35 is being withdrawn from around the collagen plug by the retraction assembly 38.

The housing assembly 35 includes an elongate cylindrical body 45 with a hand grip 46 on one end thereof. The body defines an introducer passage 48 seen in FIG. 2 centrally therethrough that receives the introducer assembly 36 therein. A side slot 49 is defined through the wall of the body 45 and extends lengthwise of the body in alignment with the hand grip 46 for the manually engageable portion of the retraction mechanism to extend for manipulation.

The introducer assembly 36 includes a thin wall insertion barrel 50 slidably mounted in the body 45 of the housing assembly 35. The barrel has a projecting end 51 thereon that is inserted into the access passage AP and an opposite rear end. The barrel 50 defines a collagen plug receiving passage therein and is provided with an inwardly directed flange 52 at the rear end thereof. The barrel 50 has a length sufficient for the barrel to project from the body 45 far enough for the barrel to extend along the access passage AP to the wall of the blood vessel BV. The barrel 50 is slidably mounted over a locator plunger 55 carried by the body 45 of the housing assembly 35 to maintain the collagen plug in place as the installation barrel 50 is being retracted. The plunger 55 has an enlarged head 56 on the projecting end thereof which fills the cross-sectional space in the plug receiving passage under the flange 52 when the barrel is fully extended. The smaller diameter support shaft 58 of the plunger 55 slidably extends through the opening in the flange 52 and is attached to the rear end of the body 45. Thus, as the barrel 50 is pulled back along the plunger 55, the head 56 of the plunger holds the collagen plug in a fixed position with respect to the housing assembly 35 as will become more apparent. The projecting face of the head 56 is spaced from the projecting end of the barrel 50 a distance substantially equal to the length of the collagen plug 12 when the barrel 50 is fully extended from the body 45 with the flange 52 on the barrel 50 against the rear annular face of the head 56 to insure that the plug will be properly in position.

The retraction mechanism 38 is attached to the barrel 50 and projects through the slot 49 through the body 45. The mechanism 38 may be any convenient arrangement which can retract the barrel 50 into the body 45. The mechanism 38 illustrated as an example includes a connector ring 60 attached to the rear side of the flange 52 on the barrel 50 to slide in the passage 48 with the barrel and a manually engagable actuator member 61 attached to the ring 60 and projecting out through the slot 49 to be manually engaged and pulled back toward the hand grip 46 pulling the barrel 50 therewith. The actuator member 61 is resiliently connected to the ring 60 so that it is urged away from the ring and is equipped with a ratchet pawl 62 that prevents the ring 60 and thus the barrel 50 from moving toward the trailing end of the body 45 until the actuator member 61 is pulled back toward the hand grip 46. This action pivots the actuator member 61 and the ratchet pawl 62 out of engagement with the wall of the body 45 to release the barrel 50 for retraction.

The applicator 14 has a prescribed overall length $L_1$ when the barrel 50 is extended. This length cooperates with the control member 20 to let the physician know when the projecting end 51 of the barrel 50 is located at the blood vessel wall BVW. The control member 20 is marked with appropriate indicia 65 that will be exposed at the trailing end of the applicator 14 when the projecting end of the barrel and thus the collagen plug is located at the exterior end of the puncture BVP through the wall of the blood vessel. Any appropriate indicia may be used, however, for purposes of illustration, the indicia 65 is shown is a safety band 66 spaced so that, as long as the safety band 66 is visible on the trailing end of the applicator 14, the leading end of the collagen plug 12 is located in the vicinity of the exterior end of the puncture BVP. To prevent overinsertion of the collagen plug 12 into the puncture, a warning band 68 is positioned inboard of the band 66 so that, if the band 68 is visible, the plug 12 is overinserted into the puncture BVP.

The interconnect assembly 39 is mounted on the housing assembly 35 and serves to grip the control member 20 on the sealing assembly 11 to interrelate the position of the applicator with the control member. The interconnect assembly 39 has a one way gripping arrangement 70 with appropriate ratchet teeth that permit the arrangement 70 and tamponading member 21 to move toward each other as the arrangement 70 slides along the control member 20 but prevents motion in the opposite direction. Thus, once the applicator 14 is on the control member 20, it can only be slipped toward the tamponading member 21. This serves to hold the housing assembly 35 substantially fixed with respect the control member and thus the tamponading member 21 while the barrel 50 is being retracted.

The interconnect assembly 39 also has a tightening arrangement 71 which slightly tightens the tamponading member 21 against the inside end of the puncture BVP while the barrel 50 is being withdrawn from around the collagen plug 12. The tightening arrangement 71 is connected to the retraction mechanism 38 and the gripping arrangement 70 so that the gripping arrangement 70 is moved with the barrel 50 when the barrel initially moves. The arrangement 71, however, releases the retraction mechanism 38 after the gripping arrangement 70 has moved the control member 20 a prescribed short distance which insures that the puncture BVP remains closed but insufficient to pull any portion of the tamponading member 21 through the puncture BVP.

The tightening arrangement 70 includes an extension 75 on the connector 60 that projects rearwardly along the passage 48 to the rear end of the body 45. The rearwardly projecting end of the extension 75 has a detent engaging cavity 76 therein. The forwardly projecting portion of the gripping arrangement 70 is connected to a resilient extension 78 with a detent 79 thereon that fits into the cavity 76 of the extension 75. The natural resiliency of the extension 78 urges the detent 79 inwardly out of the cavity 76 to disconnect the extension 78 from the extension 75. The passage 80 through the end of the body 45 keeps the detent 79 and cavity 76 forced together until the forwardly projecting end of the extension 78 moves into registration with a release cavity 81 in the body 45 opening into the passage 80. This releases the gripping arrangement 70 from the extension 75 on the tightening arrangement 70 and also holds the gripping arrangement 70 in a fixed position with respect to the body 45 while the extension 75 continues to move with the retraction of the barrel 50.

The locator mechanism 40 includes a locator pad 85 defining a central passage therethrough to the slidably fit over the barrel 50. A tubular member 86 is attached to the pad 85 and extends over the forward end of the body 45. The member 86 is divided into rearwardly directed resilient strips 88 that are equipped with inwardly facing one way grippers that cooperate with complementary grippers 89 on the outside of the body 45. The grippers are arranged to permit the locator mechanism 40 to be moved out over the barrel 50 until the pad 85 is against the skin but prevents movement in the opposite direction. This provides a secondary method for locating the applicator 14 with respect to the blood vessel wall puncture BVP.

To compensate for any loss of volume in the collagen plug 12 as it becomes a gelatinous mass, a compensator assembly 90 is provided. While different mechanisms may be used, the assembly 90 shown for purposes of illustration is mounted in the projecting end of the enlarged head 56 on the plunger 55 and is activated as an incident to the retraction of the barrel 50 off of the collagen plug 12. The assembly 90 includes a pusher plate 91 with a support tube 92 slidably extending into an annular passage in the head 56 and opening onto the end thereof. The plate 91 is urged out of the head 56 by a spring 94 captured between the end of the tube 92 and the bottom of the passage. The tube 92 has a limiting stop on it to limit the extension of the plate 91 away from the end of the head 56. The amount of possible extension from the head 56 is selected to correspond to the plug volume lost as the plug softens. The strength of the spring 94 is limited so that the plate 91 will not force the plug 12 through the puncture BVP. The plate 91 is held in the retracted position until the barrel 50 releases the plug by the friction between the plug and the barrel 50.

Method of Use

Figure 5:
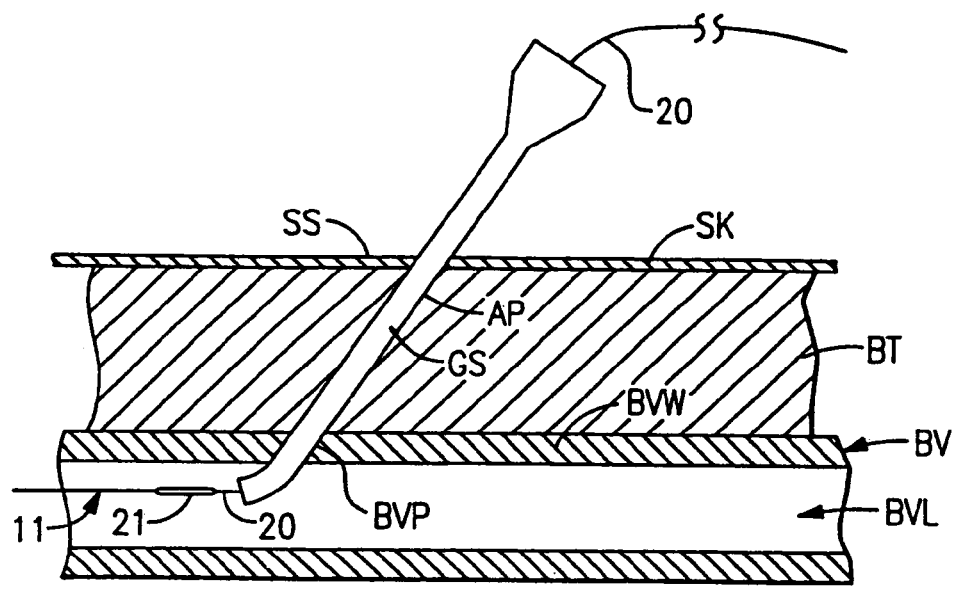
FIGS. 5-9 illustrate one embodiment of the method of the invention.

The method of sealing a blood vessel using the first embodiment of the invention is illustrated in FIGS. 5-9. As seen in FIG. 5, the temporary sealing assembly 11 is installed while the introducer guide sheath GS is still in position. The temporary sealing assembly 11 is installed by threading the projecting end 22 thereof down through the guide sheath GS and into the blood vessel lumen BVL. The control member 20 is threaded through the guide sheet GS until the collapsed tamponading member 21 passes into the blood vessel lumen BVL as seen in FIG. 5. Thereafter, the tamponading member 21 is expanded to its expanded condition with the syringe 26 and the guide sheath GS is removed. The physician physically pulls back on the control member 20 so that the expanded tamponading member 21 is pulled back up against the inside end of the puncture BVP through the blood vessel wall. The tamponading member 21 is illustrated in the sealing position in FIG. 6.

Figure 6:
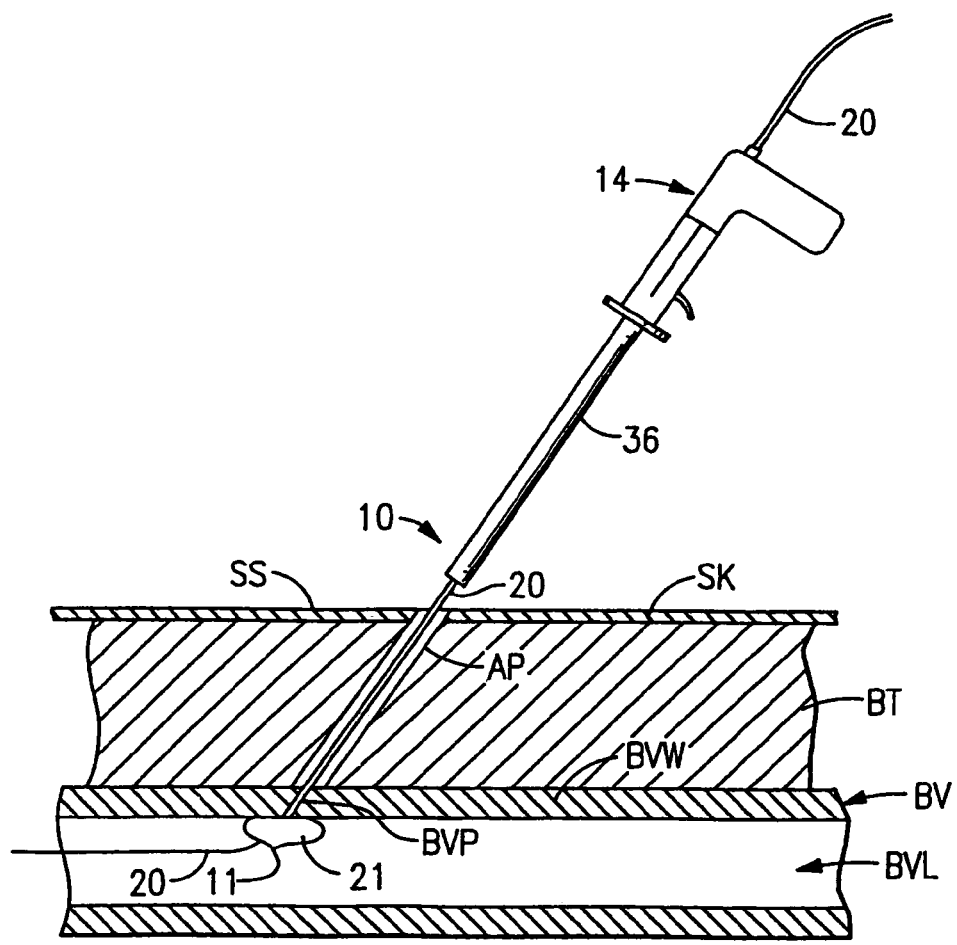
Figure 7:
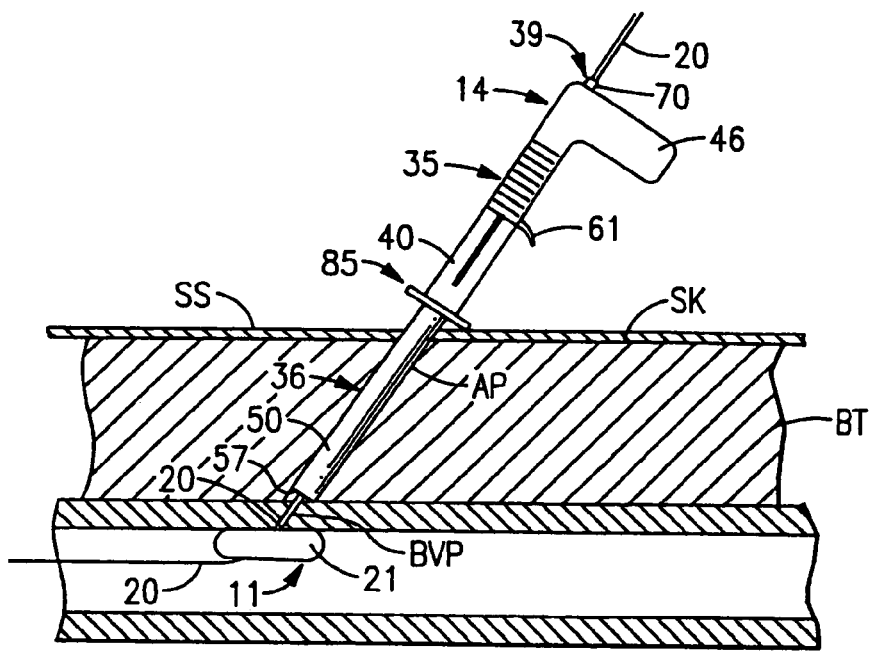

After the tamponading member 21 is pulled up against the inside end of the puncture BVP, the applicator 14 with the collagen plug 12 therein is inserted over the exterior end 24 of the control member 20 so that the applicator and collagen plug is slipped toward the patient's skin. It will be appreciated that the physician holds the control member 20 to maintain the pressure of the tamponading member 21 against the inside end of puncture BVP at all times. After the applicator and collagen plug are inserted over the control member 20 as seen in FIG. 6, the physician carefully slides the applicator 14 along the control member 20 so that the insertion barrel 50 on the introducer assembly 36 passes into the access passage AP through the skin and tissue. The physician continues to push the applicator 14 toward the patient while holding the control member 20 to keep the tamponading member 21 in place until the safety band 66 of the indicia 65 on the control member 20 becomes visible at the trailing end of the applicator 14. At this time, the projecting end 51 of the barrel 50 is located in the vicinity of the outside end of the puncture BVP through the blood vessel wall BVW as seen in FIG. 7.

Figure 8:
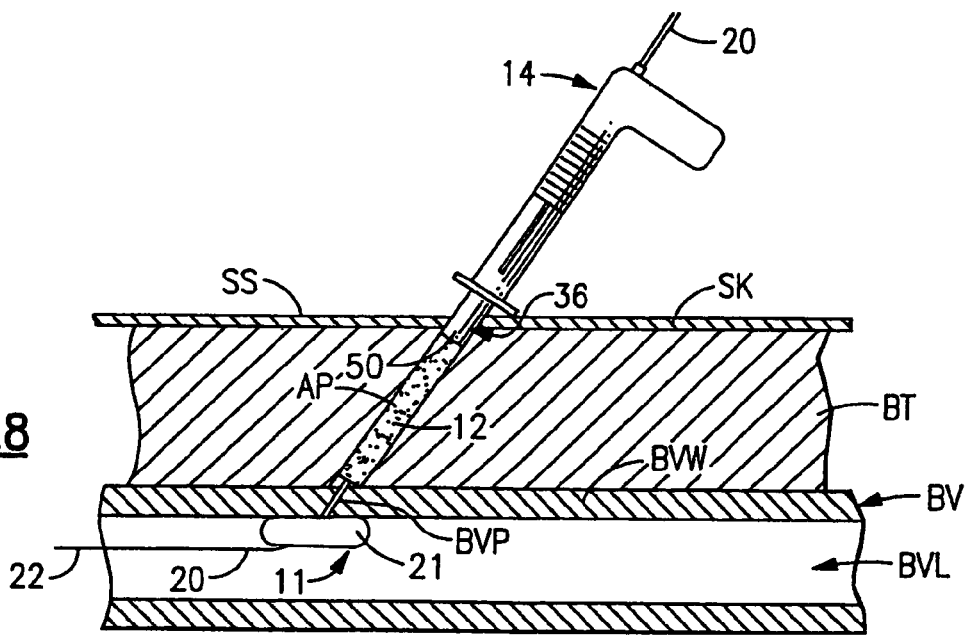
Figure 9:
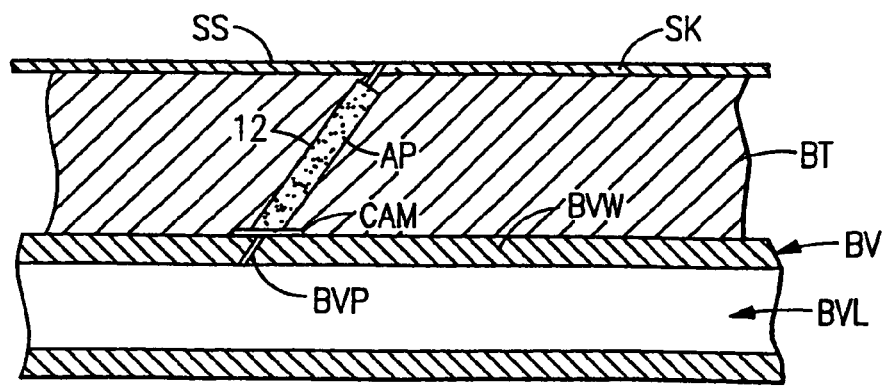

Since the one way gripping arrangement 70 of the interconnect assembly 39 prevents the applicator 14 from being moved back up the control member 20, the collagen plug carried in the end of the barrel 50 is positively located with respect to the blood vessel wall puncture BVP. The physician then slides the locator mechanism 40 out along the body 45 until the locator pad 85 lies at the skin surface SS. This serves to stabilize the applicator 14 and also to act as a secondary reference to locate the applicator 14 with respect to the outside end of the blood vessel wall puncture BVP as is also shown in FIG. 7. The barrel 50 is now ready to be withdrawn from around the collagen plug 12 since the housing assembly 35 is fixed relative to the control member 20. The housing 35 remains stationary while the physician pulls the actuator member 61 back toward the hand grip 46. This serves to retract the barrel 50 while leaving the housing assembly 35 in place so that the locator plunger 55 holds the collagen plug 12 in place. Although the barrel 50 does not have to be fully retracted before the procedure is completed, it typically is fully retracted as seen in FIG. 8 to leave the plug 12 in position in the access passage AP. As soon as the body fluids contact the plug 12, it starts to soften and any seepage of blood through the blood vessel puncture BVP serves to start the formation of a coagulum at the exterior end of the puncture BVP. Typically, the applicator 14 is left in position while the tamponading member 21 is collapsed back to its original position and the control member 20 pulled to pull the tamponading member 21 back through the collagen plug 12 into the applicator 14. By having a projecting end 22 on the control member 20 long enough to still reach into the blood vessel lumen BVL with the tamponading member 21 within the applicator 14, contact is not lost with the blood vessel lumen if something causes the collagen plug 12 not to properly seal. This will facilitate re-access to the blood vessel lumen BVL. After the physician checks to see if the seal has been affected, the projecting end of the control member 20 can be pulled out through the collagen plug 12 to complete the procedure and leave the collagen plug 12 in place forming the coagulum CAM as seen in FIG. 9.

Alternate Embodiment of Sealing Assembly

FIG. 10 shows an alternate embodiment of the sealing assembly which has been designated as 111. The sealing assembly 111, like the sealing assembly 11, has an elongate flexible control member 120 with an expandable tamponading member 121 mounted on the control member 120. In addition to the inflation lumen 128 which is provided through the control member 120, an injection lumen 132 is provided along the length of the control member 120 and exits the control member 120 adjacent the trailing end of the tamponading member 121 that faces the blood vessel wall puncture BVP. The size of the discharge port 134 through which the injection lumen exits is selected to have a longitudinal length $L_1$ as seen in FIG. 10. The length $L_1$ is selected to be less than the thickness of the blood vessel wall BVW at the puncture BVP. An appropriate injection port (not shown) to the injection lumen 132 is provided in the exterior end of the control member 120.

This allows the physician to inject a detectable fluid through the injection lumen 132 and out the port 134 as the expanded tamponading member 121 is pulled back toward the puncture BVP. The physician can monitor the flow of the protectable fluid along the blood vessel lumen BVL with appropriate equipment such as fluoroscopy. The physician continues to pull the tamponading member 121 toward the wall BVW until the flow of the detectable fluid along the lumen BVL is stopped. This ensures that the tamponading member 121 does not hang up on occlusions or plaque within the blood vessel lumen and not seat good against the blood against the blood vessel wall BVW.

Second Embodiment of Applicator

The second embodiment of the applicator is designated 114 and is illustrated in FIGS. 11-15. The basic difference between the applicator 114 and the applicator 14 is that the applicator 114 has an open section through which the control member on the temporary sealing assembly can be installed without feeding the control member axially through the collagen plug and applicator. The applicator 114 like the applicator 14, includes a housing assembly 135, and introducer assembly 136, a retraction mechanism 138, an interconnect assembly 139, and a locator mechanism 140. These assemblies and mechanisms operate similarly to the corresponding assemblies and mechanisms of the first embodiment of the invention.

The cylindrical body 145 defines a V-shaped cutout 147 therein down to the passage through which the control member on the temporary sealing assembly passes so that control member can be laid into the passage as it is being operated to install the collagen plug. The insertion barrel 150 of the introducer assembly 136 is slit at 141 along its length and the sidewall thereof is turned slightly inwardly so that the control member on the temporary sealing assembly can be pressed therethrough. This slit 141 is also defined through the inwardly directed flange 152. The locator plunger 155 is provided with a V-shaped cutout 142 that extends from the central passage through which the control member passes to the exterior surface thereof. Similarly, the gripping arrangement 170 on the interconnect assembly 139 is provided with a V-shaped cutout 143 to allow the control member to be placed laterally into the passage up through the arrangement 170. It will be appreciated that the arrangement 170 still is able to grip the control member during use as with the first embodiment of the invention. Likewise, the locator pad 185 and tubular member 186 have a V-shaped cutout 144 to allow the control member to pass through the center thereof. The body 145 is provided with a closure 195 that closes the rear portion of the cutout through the body 145 to keep the control member in place once it is placed in the central passage running through the applicator.

The collagen plug 112 used with the second embodiment of the applicator is illustrated in FIGS. 12 and 15 and includes a thin V-shaped cutout 196 which extends to the central passage through the plug 112 to receive the control member of the temporary sealing arrangement. While the plug 112 may work with a single V-shaped cutout 196, it is illustrated with a wider opening section 198 adjacent the exterior surface thereof to facilitate placement of the control member therein. It will be noted that the cutout comes together just before the central passage through the plug 112 is reached so that, once the control member is snapped into the passage through the plug, it is retained therein.

Third Embodiment of the Invention

Figure 16:
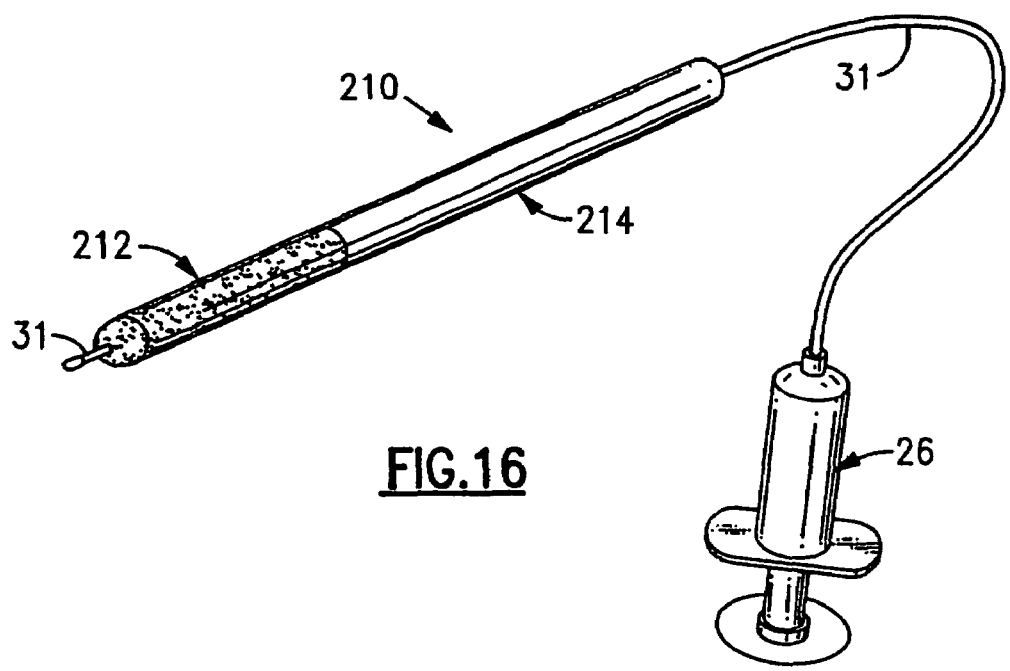
FIG. 16 is a perspective view of a third embodiment of the invention.
Figure 17:
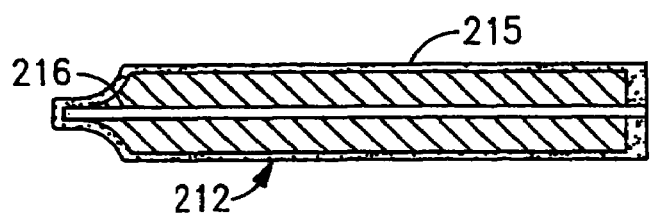
FIG. 17 is a longitudinal cross-sectional view of the collagen plug of the third embodiment of the invention.

FIGS. 16 and 17 illustrate a third embodiment 210 of the invention which includes a collagen plug 212 and an applicator tube 214. The collagen plug 212 is installed on the control member and the extension 31 to the syringe 26 as described with the first embodiment of the invention. The applicator tube 214 is a cylindrical tube defining a central passage therethrough to just slidably receive the control member of the temporary sealing arrangement. The physician simply slides the collagen plug 212 and the tube 214 onto the control member of the temporary sealing arrangement so that the leading end of the collagen plug 212 faces the access passage AP in the patient. The physician then uses the applicator tube 214 to push the collagen plug 212 down to the outside end of the puncture BVP. The combined overall length of the collagen plug 212 and the applicator tube 214 corresponds to that of the first embodiment of the invention so that the physician can use the indicia 65 on the temporary sealing assembly to determine when the leading end of the collagen plug 212 is located in the vicinity of the outside end of the puncture BVP.

The collagen plug 212 is made so that an outside layer 215 thereon has a prescribed spring and softening rate so that the plug 212 will not soften prior to being fully inserted into the access passage AP. The tapered leading end 216 on the collagen end 212 serves to keep the collagen plug centered in the access passage AP and open it up to receive the plug 212. The higher strength at the trailing end of the collagen plug 212 permits the applicator tube 214 to push it into place before the plug softens.

Fourth Embodiment of the Applicator

Figure 18:
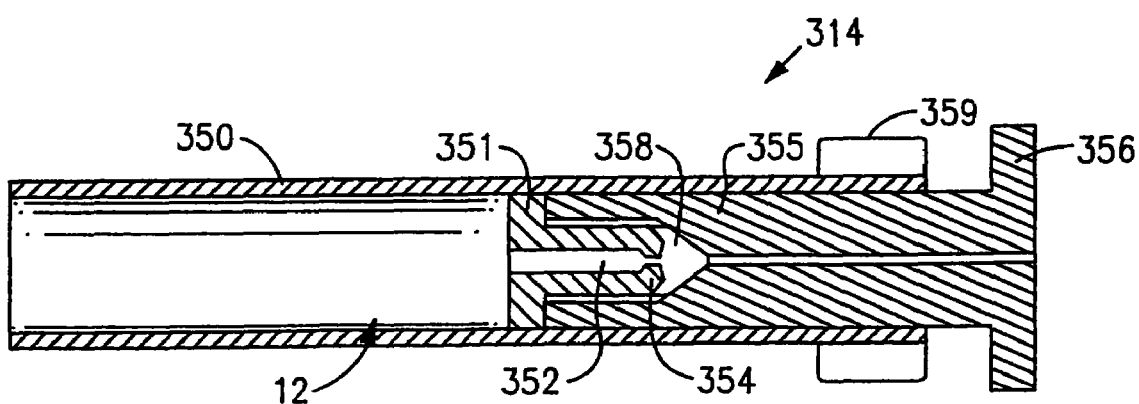
FIG. 18 is a longitudinal cross-sectional view of another embodiment of the invention.

FIG. 18 illustrates an alternate embodiment of the applicator which has been designated by the reference of 314. The applicator 314 include an insertion barrel 150 with the projecting end 351 thereon adapted to be inserted into the access passage AP in the patient. The barrel 350 defines an internal passage therethrough adapted to slidably receive the collagen plug 12 therein. A one-way check member 353 is mounted in the barrel 350 behind the plug 12 and has a face thereon abutting the plug 12 to maintain it lengthwise of the barrel 350 as will become more apparent. The check member 353 defines a tamponading member receiving chamber 352 which opens onto the trailing end of the plug 12 and trailing end of the check member 353 is provided with a one-way gripping assembly 354 which grips the control member of the temporary sealing arrangement to allow the check member 353 to be moved along the control member toward the expanded tamponading member but prevents movement of the check member 353 in the opposite direction. A locator plunger 355 extends into the barrel 350 behind the check member 353 to maintain the check member 353 in position relative to the collagen plug 12 as the collagen plug 12 is being installed. An appropriate drive flange 356 is provided on the trailing end of the plunger 355 projecting out of the barrel 350 to be manually engaged. The leading end of the plunger 355 is counterbored at 358 to receive the projecting portion of the check member 353 therein so that the leading end of the locating plunger abuts the back side of the check member 353. The holding ring 359 is provided on the trailing end of the barrel 350 so that the physician can hold both the flange 356 and the ring 359 to simultaneously push both the plunger 355 and the barrel 350 into the access passage AP. As soon as the leading end of the collagen plug 112 is located in the vicinity of the outside end of the puncture BVP, the barrel 350 can be withdrawn from around the collagen plug 12 simply by pulling out on the plunger 356 and the member 353. This is because the check member 353 prevents the collagen plug 12 from being withdrawn with the barrel 350. After the collagen plug 12 is installed and the temporary sealing assembly is ready to be withdrawn, the physician can hold the back side of the plug 12 while the collapsed tamponading member 21 is pulled through the plug 12 into the recess 352. Because the projecting end 22 on the control member 20 is smaller than the collapsed tamponading member 21, the rest of the control member can be pulled out of the plug 12 without damaging the plug.

What is claimed as invention is:

1. An apparatus for sealing a puncture made through the skin and body tissue of a patient into a body cavity having a wall, said apparatus comprising:
   a. a temporary locating assembly comprising
      i) an elongate control member having a length greater than the length of the puncture to be sealed and a cross-sectional size smaller than the width of the puncture so that said control member passes freely through the puncture, said control member having an indicator means control therewith,
      ii) an expandable member fixedly mounted on said control member at a first prescribed location axially of said control member so that a portion of said control member extends exteriorly of the patient when said expandable member is located within the body cavity, said expandable member having a collapsed condition narrower in width than the width of the puncture for passage of said collapsed expandable member through the puncture into the body cavity and an expanded condition larger in width than the width of the puncture to prevent passage of said expandable member when in an expanded configuration through the puncture so that said control member can be used to pull said expanded expandable member in the body cavity up against that end of the puncture opening into the body cavity to locate said expanded expandable member at the end of the puncture, and
      iii) positioning indicia at a prescribed first position on said control member where said prescribed first position is located at a first prescribed distance from that portion of said expanded expandable member contacting the edge of the body cavity at the end of the puncture sufficiently great for the indicia to be located outside the patient; and,
   b. an applicator comprising
      i) an introducer member defining a projecting end thereon and an opening therethrough through which said control member can pass, and
      ii) an indicator located a second prescribed distance from said projecting end of said introducer member, said second prescribed distance being a prescribed small amount less than said first prescribed distance so that, when said introducer member of said applicator is inserted over said control member while said expandable member is expanded and pulled up against that end of the puncture opening into the body cavity using said control member, and said applicator is moved along said control member until said indicator is aligned with an indicator means on said control member, there is a positive indication that said projecting end of said introducer member is located inside the puncture in the vicinity of the end of the puncture opening into the body cavity but spaced from the end of the puncture by said prescribed small amount to insure that the projecting end of said introducer member is not projecting into the body cavity.

* * * * *